United States Patent [19]

Clements

[11] 4,239,494

[45] Dec. 16, 1980

[54] PHASE SEPARATOR FOR CONTINUOUS-FLOW ANALYTICAL SYSTEMS

[75] Inventor: John A. Clements, Wallington, England

[73] Assignee: Technicon Instruments Corporation, Tarrytown, N.Y.

[21] Appl. No.: 954,000

[22] Filed: Oct. 23, 1978

[30] Foreign Application Priority Data

Oct. 25, 1977 [GB] United Kingdom ............... 44420/77

[51] Int. Cl.$^2$ ............................................ G01N 33/16
[52] U.S. Cl. ................................... 23/230 R; 422/82; 210/108
[58] Field of Search ................. 23/230 R; 422/82, 81; 210/108, 23 C

[56] References Cited

U.S. PATENT DOCUMENTS

| 2,990,238 | 6/1961 | Kabisch et al. | 210/82 |
| 3,211,645 | 10/1965 | Ferrarl | 422/82 |
| 3,618,747 | 11/1971 | Thummel | 210/82 |
| 3,868,322 | 2/1975 | Orloff | 210/108 |

Primary Examiner—William F. Smith
Attorney, Agent, or Firm—S. P. Tedesco

[57] ABSTRACT

A separator and method, particularly for use in continuous-flow analysis, for separating liquid from a mixture of a liquid phase and a solid phase. The separator includes a first conduit, and a second conduit which communicates with the first conduit across a filter, whereby liquid in the liquid-solid phase mixture in the first conduit can be pumped into the second conduit, the solid phase being held back by the filter, the filter then being back-washed with wash liquid. The liquid-solid phase mixture may be segmented, the segments being separated by occluded air, or air and wash liquid segments, the back-washing then being controlled to occur while the air and/or wash liquid traverses the filter.

12 Claims, 5 Drawing Figures

PHASE SEPARATOR FOR CONTINUOUS-FLOW ANALYTICAL SYSTEMS

This invention relates to apparatus and techniques useful in continuous-flow analytical systems for effecting, in positive fashion, a separation of solid and liquid phases in a flowing stream.

In the developing technology for analyzing liquid samples, one constituent to be reacted is bound, or immobilized onto particulate matter, e.g., latex particles, to facilitate separation of the reaction product formed therewith. For example, in performing radioimmunoassays, the concentration of antigen in a sample is determined as a result of the competitive reaction between such antigen and a known quantity of labelled antigen introduced into the sample with immobilized antibody. The determination can be made either by direct analysis of the reaction product immobilized on the latex particles, i.e., the solid phase, or the remaining reaction mixture, i.e., the liquid phase or supernatant, following separation of the solid and liquid phases. To achieve accurate analysis, it is essential that a complete separation of the solid and liquid phases be effected.

In "Magnetic Solid Phase Radioimmunoassay" by L. S. Hirsch and S. Yaverbaum, *Clin. Chem. Acta* Vol. 63, (1975) pp. 69–72, a radioimmunoassay is described, wherein the antibody is immobilized onto magnetic particles (solid phase); which are introduced into a sample containing an unknown concentration of the antigen to be measured and a known concentration of a same antigen which has been radioactively labelled. The described technique is carried out in a testtube reactor and the solid and liquid phases are separated by a magnetic field. The liquid-phase is decanted and assayed.

Also, in co-pending U.S. Ser. No. 776,443, now U.S. Pat. No. 4,141,687 a continuous-flow system for performing radioimmunoassays is described, wherein magnetic particles are again used to define the solid phase. In such system, following the competitive reaction, the solid phase is magnetically trapped in on-line fashion at one portion of the conduit system. While magnetically trapped, the solid phase is washed by passages of a wash liquid along the system, so as to remove all traces of the liquid phase therefrom. In such system, either the solid or liquid phase can be introduced.

An object of this invention is to provide apparatus for the positive on-line separation of solid and liquid phases in continuous-flow systems.

Another object of this invention is to provide, in a continuous-flow system, an on-line separator for separating solid and liquid phases, which is reliable in operation and inexpensive in cost.

The present invention concerns a separator for use in continuous-flow systems, for effecting the separation of solid and liquid phases contained in a flowing stream. More specifically, there is provided a separation device comprising a first conduit along which successive samples, each separated conventionally by wash liquid and air segments including solid and liquid phases, are directed as a stream and a second off-take conduit. The off-take leg as provided is connected, preferably, at right angles to the first leg. The inlet of the off-take leg includes a frit, or filtering element, effective to pass only the liquid phase. Such frit can be formed of glass particles which have been sintered together. During passage of each sample over the frit, differential positive pumping along the first and second conduits ensures the separation of part of the liquid phase along the second conduit. Also, the direction of the fluid flow along the first conduit is preferably downward in a vertical direction, whereby the normal tendency of the solid phase is to bypass the frit. Additionally, the internal cross-section of the first conduit adjacent the frit is reduced to accelerate passage of the liquid phase past the frit and to press the air bubbles separating successive liquid segments in the flowing stream against the frit, so as to scrub the surface portions thereof clean of the solid phase. Additionally, to ensure non-clogging of the frit, such frit is reversed-flushed while the wash liquid segments in the flowing stream are passing over the frit, between the passage of the liquid phases in successive samples through the frit.

A BRIEF DESCRIPTION OF THE DRAWINGS

Figure 1:
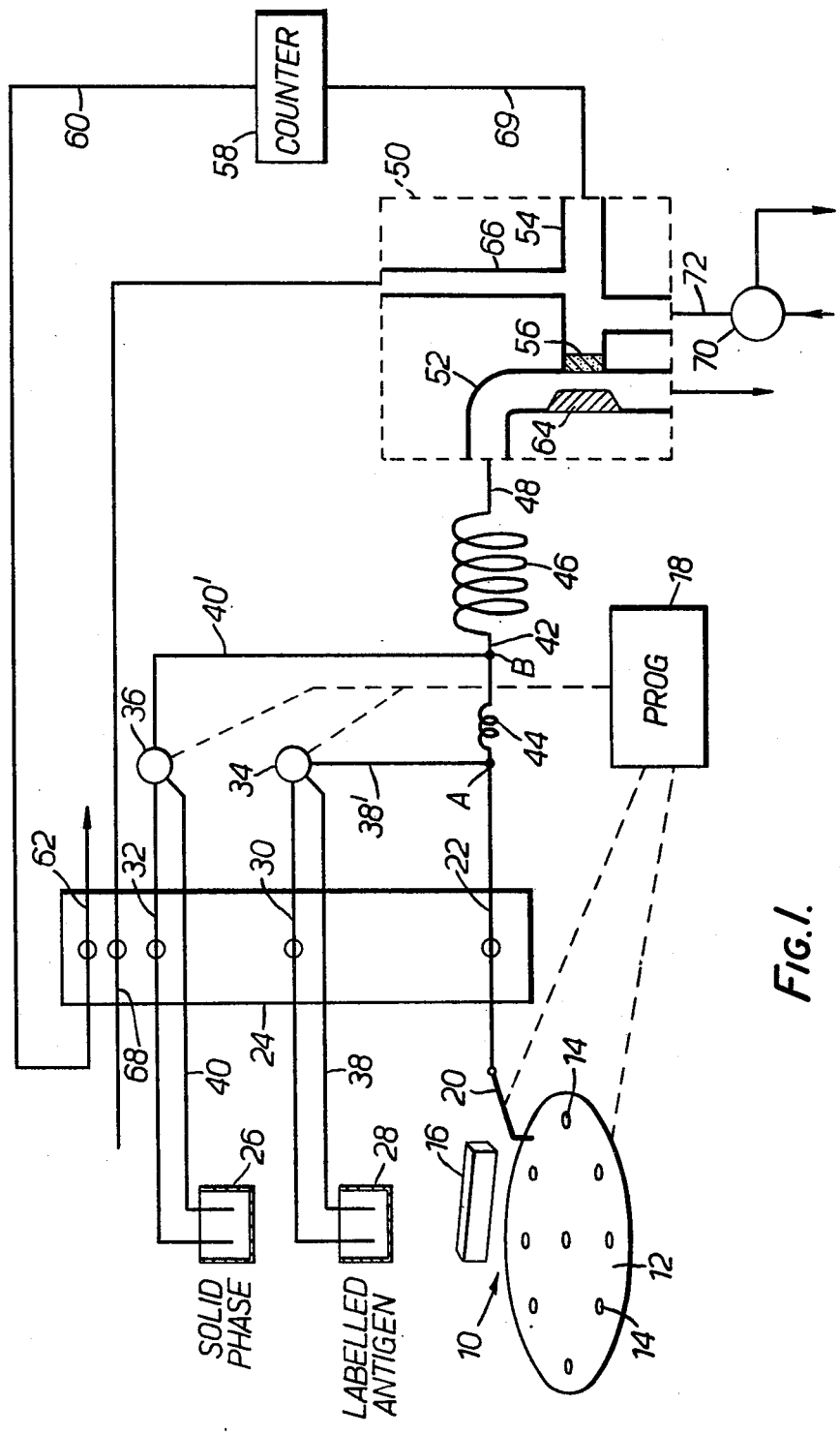
FIG. 1 shows a flow diagram of a continuous-flow system for performing radioimmunoassays and illustrating the novel separator of the present invention.
Figure 2:
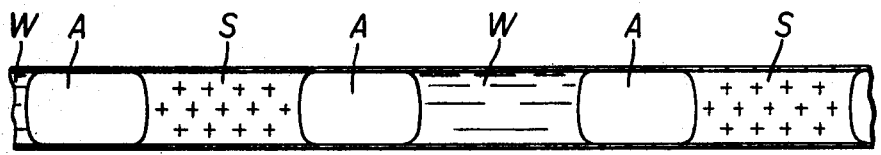
FIG. 2 illustrates the composition of the gas-segmented liquid stream passing along the continuous-flow system of FIG. 1, prior to phase separation.

Referring now to the drawings, FIG. 1 illustrates a continuous-flow system for performing radioimmunoassays, which is of the type described in co-pending U.S. Ser. No. 776,443. Such system comprises a sampler arrangement 10, for directing, as a flow stream, successive samples to be analyzed. Sampler arrangement 10, which may be of the described in U.S. Pat. No. 3,038,340, comprises a turn-table 12 supporting a plurality of sample receptacles 14 and a laterally disposed wash liquid reservoir 16. Turn-table 12 is controlled by a programmer 18 to be indexed incrementally, to present each sample receptacle 14 at a take-off station disposed beneath probe 20. The outlet of probe 20 is connected to the inlet of pump tube 22 incorporated in peristaltic-type pump 24, of the tybe described in U.S. Pat. No. 2,935,028. Probe 20 is controlled by programmer 18 to be immersed into each sample receptacle 14 advanced to the take-off station and, alternately, into wash reservoir 16. As probe 20 aspirates air between immersions into successive sample receptacles 14 and, alternately, into wash reservoir 16, the sample stream directed along pump tube 22 comprising successive liquid samples S, each separated from adjacent samples by successive air, wash liquid and air segments, as shown in FIG. 2. Accordingly, the integrity of each sample S is maintained during flow along the entire system, as hereinafter described. In addition, a source 26 of antibodies immobilized onto the surface of latex particles, defining the solid phase, and a source 28 of labelled antigen is provided. The labelled antigen source 28 and the solid phase source 26 are connected to the inlets of pump tubes 30 and 32, respectively, in peristaltic pump 24.

As described in co-pending U.S. Ser. No. 776,443, the solid phase from source 26, appropriately buffered, and labelled antigen from source 28, appropriately buffered, are introduced into the sample stream in controlled discrete volumes and in proper phase, so as to be admixed with the successive samples passed along pump tube 12. To this end, shunt valves 34 and 36 are connected to the outlets of pump tubes 30 and 32, respectively. Each shunt valve 34 and 36 comprises a single-input, three-port structure, the inputs being connected directly to the outlets of pump tubes 30 and 32, respectively. One output port of shunt valve 34 and one output port of shunt valve 36 are connected along conduits 38 and 40, respectively, so as to provide a return path to the corresponding sources 28 and 26. The remaining output port of shunt valve 34 and the remaining outlet port of shunt valve 36 are connected along conduits 38 and 40 at Junctions A and B, respectively, with conduit 42, connected to the outlet of pump tube 22. Shunt valves 34 and 36 are operated by programmer 18, such that proper discrete volumes of labelled antigen and solid phase, respectively, are introduced at Junctions A and B into each successive sample passing along conduit 42. Mixing coil 44 is disposed along conduit 42, between Junctions A and B, to ensure propoer mixing of the labelled antigen within the sample prior to introduction fo the solid phase.

Accordingly, the flowing stream passing from Junction B along conduit 42, as shown in FIG. 2, comprises liquid sample segments S, each containing the solid phases, as indicated by "+". The flowing stream, including the solid phase, is passed through incubation coil 46, which enables the reaction to proceed. During the reaction, there is competition between the labelled antigen (introduced at Junction A) and the antigen in a sample S to be analyzed with the antibodies immobilized on the latex particles. The proportion of labelled antigen, since it is introduced in controlled volume, which binds to the solid phase, or, alternately, remains unbound in the liquid phase, provides an indication of the total concentration of antigen originally present in the sample S. The reaction mixture passes through coil 36 and along conduit 48 to separator 50 of the present invention, to effect separation of the solid and liquid phases and subsequent measurement of the liquid phase, as to be described.

As illustrated, separator 50 comprises a conduit 52 connected to the outlet of conduit 48 and having an outlet passing to waste. An off-take conduit 54 is connected along the length of conduit 52, which includes a frit 56 located at its inlet end. Frit 56 can be formed of any material which is inert with respect to the mixture stream passing along conduit 52 and having an effective pore size only the liquid phase (supernatant) along off-take conduit 54. The outlet of off-take conduit 54 is connected along conduit 69 to the inlet of scintillation counter 58, which measures the labelled unbound antigen remaining in each sample S, following separation of the solid phase, as described. The outlet of counter 58 is connected along conduit 60 to pump tube 62 incorporated in pump 24. Accordingly fluid is positively pumped through frit 56, at a precisely controlled rate, by the action of pump tube 62. The outlet of pump tube 62 is passed to waste.

As shown in FIG. 2, the sample stream comprises a series of liquid samples S containing a solid phase indicated the "+" carried along in suspension. Preferably, the solid phase has a specific gravity approaching that of the liquid phase, such as not to tend to settle out, either by flotation or gravitation, during passage along the system. Hence, the wash of the system is not deterioriated, i.e., there is no contamination between successive samples S. For example, if the solid phase were to settle out, either by flotation or gravitation, the possibility of the particles passing, either over or under, the upstream air bubbles A and upstream wash liquid W to contaminate the next upstream liquid sample S would be substantially increased.

Figure 3A:
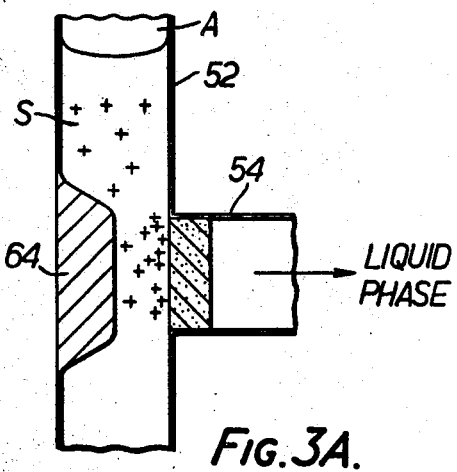
FIGS. 3A–3C illustrate the operation of the separator of the present invention in separating the solid and liquid phases in the liquid stream illustrated in FIG. 2.
Figure 3B:
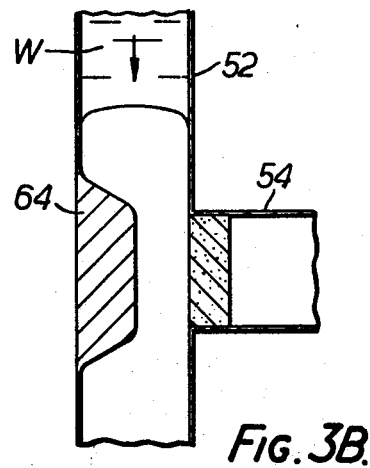

The cross-sectioned area of conduit 50 adjacent frit 56 is reduced, as by a protuberance 64, as more particularly illustrated in FIGS. 3A–3B. Also, the flow direction along conduit 52 and over protuberance 64 is downward, so as to assist in the separation of the solid phase.

It is to be noted that a positive pumping action is effected along conduit 52, due to pump tubes 22, 30 and 32 and also, along off-take conduit 54 by pump tube 62. Protuberance 64 is preferably designed, such that the effective flow rate between such protuberance and frit 56 is substantially equal to the flow rate of the solid phase along conduit 52. Also, the flow rate through frit 56, as determined by pump tube 62, removes a volume of liquid at least sufficient to effect analysis of the sample. Therefore, because of differential pumping action, positive separation of the solid phase along conduit 52 and the liquid phase along off-take conduit 54 can be achieved.

For example, FIG. 3A illustrates the liquid phase being separated through the frit 56, as indicated by the arrow. At this time, the solid phase is flowed toward and over the frit 56, falling by gravity downwardly along tube 52 to waste. At this time, the remaining liquid phase flows over the protuberance 64 to waste. Protuberance 64 serves to direct the liquid phase flow over and adjacent the surface of frit 56, so as to facilitate and accelerate separation thereof.

The separated liquid phase is passed along off-take conduit 54 and conduit 69 to counter 48. As the liquid phase is passed along conduit 54, it is re-segmented by air bubbles forcibly injected into the flowing stream along conduit 66, connected at its input end to pump tube 68 incorporated in pump 24. The resegmentation of the liquid phase prevents intermixing between successive samples passing through counter 58 to waste.

Figure 3C:
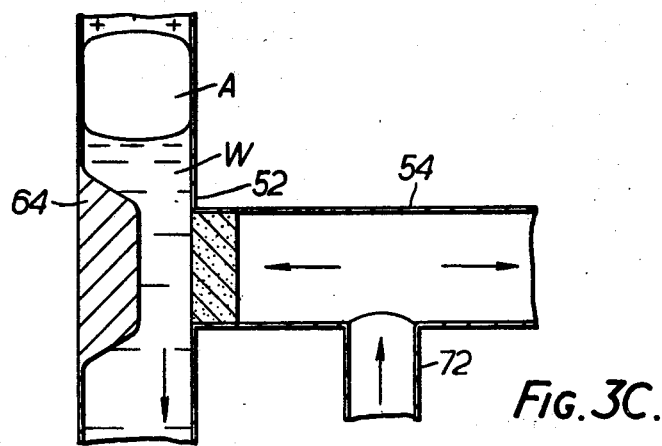

The upstream air bubble A following the sample along conduit 52 serves to clean the surface of frit 56. As shown in FIG. 3B, the air bubble A is compressed by protuberance 64, whereby air molecules are directed toward the surface of frit 56, to remove residual solid phase from over such surface; such removal is assisted by gravitational force tending to carry such particles downward along conduit 52 to waste. Also, no portion of such air bubble is pulled through frit 56. Subsequently, as shown in FIG. 3C, the upstream wash liquid segment W is passed over frit 56. At this time, programmer 18 controls single-input, three-port valve 70. One outlet of valve 70 is connected to waste and the remaining outlet is connected along conduit 72 to off-take conduit 54. The input port of valve 70 is connected to a source of wash liquid, under pressure. The wash liquid stream passed through valve 70 may be air-segmented. For example, while not illustrated, the inlet port of valve 70 can be connected to a pump tube incorporated in pump 24, whose inlet is in fluid connection with a source of wash liquid. The flow rate of wash liquid through valve 70 and along conduit 72 should be, at least, in excess of the flow rate induced along off-take conduit 54 by the action of pump tube 62, such that a portion thereof is forced backwardly, in the upstream direction, so as to reverse-flush frit 56. A portion of such wash liquid, because of the pumping action of pump tube 62, is passed along conduit 54, in the downstream direction, such as to maintain the character of the sample stream following through counter 58. Accordingly, because of the scrubbing action of the air bubbles and the reverse-flushing of frit 56, in on-line fashion, an effective separation of the solid and liquid phases of successive samples passed along the system can be achieved without contamination of successive samples. It should be evident that, because of the differential pumping action along conduits 52 and 56, along with the introduction of air bubbles along conduit 66, successive liquid phases separated through frit 56 from successive liquid samples S and directed to counter 58 for measurement are separated by a sequence of air, wash liquid and air segments.

I claim:

1. A continuous-flow analytical system, comprising:
   a first conduit for passing successive liquid samples each containing, at least, a solid phase and liquid phase, said liquid samples being separated, at least, by an occluding air segment,
   a second conduit communicating with said first conduit across a filter element;
   means for positively pumping at least a portion of said liquid phase through said filter element in a first direction and along said second conduit, said solid phase being substantially precluded from passing through said filter element,
   means for flowing a wash liquid along said second conduit and through said filter element in a second direction during passage of said air segment over said filter element to ensure non-clogging of said filter element by said solid phase, and means for analyzing said liquid phase.

2. A continuous-flow analytical system as defined in claim 1, wherein said successive liquid samples are separated by a sequence of air-wash liquid-air segments, said flowing means being operative during passage of at least one of said segments over said filter element.

3. A continuous-flow analytical system as defined in claim 1 further including means for controlling said flowing means to pass said wash liquid through said filter element in said second direction subsequent to the passage of said sample over said filter element and along said first conduit.

4. A continuous-flow analytical system as defined in claim 1 further including means connected to said second conduit for analyzing the liquid phase passed through said filter element and along said second conduit.

5. A continuous-flow analytical system as defined in claim 1 further including means connected to said second conduit for resegmenting said liquid phase passed through said filter element and along said second conduit.

6. A continuous-flow analytical system as defined in claim 1 further including indexible sampling means connected to said first conduit for passing successive liquid samples along said first conduit, said flowing means including valving means for passing wash liquid to said second conduit, and programmable means for controlling the operation of said sampler means and said valving means.

7. A continuous-flow analytical system as defined in claim 6, wherein said flowing means is operative to pass wash liquid through said filter element in said second direction and along said second conduit, whereby successive samples passing along said second conduit are separated by wash liquid segment.

8. A continuous-flow analytical system as defined in claim 1, wherein said first conduit is restricted adjacent said filter element.

9. A continuous-flow analytical system as claimed in claim 1, wherein said filter element is in the form of a frit.

10. In a method of continuous-flow analysis of successive liquid samples, each separated by, at least, an occluding air segment, which comprises forming a reaction mixture of each sample with, at least a solid phase particulate reactant, and pumping said reaction mixture along a first conduit, the improvement which comprises providing a second conduit communicating with said first conduit across a filter element, periodically positively pumping at least a portion of the liquid from the first conduit through said filter element into said second conduit, the solid phase being prevented from entering the second conduit by said filter element; subjecting said liquid portion to analysis, and periodically flowing a wash liquid from said second conduit through said filter element into said first conduit, said flow of wash liquid being controlled to occur when an air segment is in contact with said filter element to prevent clogging of the filter element by the solid phase.

11. A method according to claim 10 wherein segments of reaction mixture are separated by a sequence of air-wash liquid-air segments, and wherein said flow of wash liquid being controlled to occur when an air segment and/or a wash segment is in contact with said filter element.

12. A method according to claim 10 wherein said filter element is in the form of a frit.

* * * * *